United States Patent
Anisingaraju et al.

(10) Patent No.: US 11,599,841 B2
(45) Date of Patent: Mar. 7, 2023

(54) DATA ANALYSIS USING NATURAL LANGUAGE PROCESSING TO OBTAIN INSIGHTS RELEVANT TO AN ORGANIZATION

(71) Applicant: Saama Technologies Inc., Campbell, CA (US)

(72) Inventors: Vidya Sagar Anisingaraju, San Jose, CA (US); Haranath Gnana, San Ramon, CA (US); Ghananeel Gondhali, Fremont, CA (US)

(73) Assignee: SAAMA TECHNOLOGIES INC., Campbell, CA (US)

( * ) Notice: Subject to any disclaimer, the term of this patent is extended or adjusted under 35 U.S.C. 154(b) by 83 days.

(21) Appl. No.: 17/073,257

(22) Filed: Oct. 16, 2020

(65) Prior Publication Data

US 2021/0103865 A1 Apr. 8, 2021

Related U.S. Application Data

(63) Continuation-in-part of application No. 14/975,778, filed on Dec. 19, 2015, now abandoned, which is a continuation-in-part of application No. 14/971,885, filed on Dec. 16, 2015, now Pat. No. 10,776,359.

(60) Provisional application No. 62/124,799, filed on Jan. 5, 2015.

(51) Int. Cl.
| | |
|---|---|
| *G06F 16/33* | (2019.01) |
| *G06F 16/35* | (2019.01) |
| *G06Q 10/06* | (2012.01) |
| *G06F 16/36* | (2019.01) |
| *G06Q 10/0637* | (2023.01) |

(52) U.S. Cl.
CPC ..... *G06Q 10/0637* (2013.01); *G06F 16/3344* (2019.01); *G06F 16/355* (2019.01); *G06F 16/367* (2019.01)

(58) Field of Classification Search
None
See application file for complete search history.

(56) References Cited

U.S. PATENT DOCUMENTS

| | | | |
|---|---|---|---|
| 5,924,072 | A | 7/1999 | Havens |
| 6,512,919 | B2 | 1/2003 | Ogasawara |
| 7,483,842 | B1 | 1/2009 | Fung et al. |
| 9,053,416 | B1 | 6/2015 | De Leo |
| 9,990,356 | B2 | 6/2018 | Yoon |
| 2003/0004790 | A1 | 1/2003 | Calderaro et al. |
| 2003/0069953 | A1 | 4/2003 | Bottom |
| 2004/0249510 | A1 | 12/2004 | Hanson |

(Continued)

OTHER PUBLICATIONS

Yeo Iksu; Sentiment Bias Detection in Support of News Credibility Judgement; IEEE;2011 pp. 1-10 (Year: 2011).*

(Continued)

*Primary Examiner* — Amresh Singh
*Assistant Examiner* — Jermaine A Mincey
(74) *Attorney, Agent, or Firm* — Kang S. Lim

(57) ABSTRACT

Methods and apparatuses for generating insights for improving an organization from unstructured and structured data. Natural language processing is employed to process the aggregated data from various data sources to create topics and the features that impact the topics. These topics are then used to generate recommendations to improve customer satisfaction with the organization.

18 Claims, 9 Drawing Sheets

(56) References Cited

U.S. PATENT DOCUMENTS

| | | | |
|---|---|---|---|
| 2006/0212486 A1 | 9/2006 | Kennis et al. | |
| 2006/0229505 A1 | 10/2006 | Mundt | |
| 2006/0282302 A1 | 12/2006 | Hussain | |
| 2008/0270120 A1 | 10/2008 | Pestian | |
| 2008/0319781 A1 | 12/2008 | Stivoric | |
| 2009/0187471 A1 | 7/2009 | Beaton et al. | |
| 2009/0287642 A1 | 11/2009 | Poteet et al. | |
| 2011/0016064 A1 | 1/2011 | Barton | |
| 2012/0011077 A1 | 1/2012 | Bhagat | |
| 2012/0110071 A1* | 5/2012 | Zhou | G06Q 30/02 709/204 |
| 2012/0221486 A1 | 8/2012 | Leidner et al. | |
| 2012/0246054 A1 | 9/2012 | Sastri | |
| 2012/0296845 A1* | 11/2012 | Andrews | G06Q 40/06 705/36 R |
| 2012/0330869 A1 | 12/2012 | Durham | |
| 2013/0080184 A1 | 3/2013 | Streat | |
| 2013/0262501 A1 | 10/2013 | Kuchmann-Beauger | |
| 2013/0297543 A1 | 11/2013 | Treiser | |
| 2014/0100922 A1 | 4/2014 | Aycock | |
| 2014/0220526 A1 | 8/2014 | Sylves | |
| 2014/0379682 A1* | 12/2014 | Du | G06F 16/9535 707/706 |
| 2015/0074040 A1 | 3/2015 | Bhattacharjee | |
| 2015/0120757 A1* | 4/2015 | Gillespie | G06F 16/24578 707/748 |
| 2015/0135300 A1 | 5/2015 | Ford | |
| 2015/0310508 A1 | 10/2015 | Pattekar et al. | |
| 2016/0048648 A1 | 2/2016 | Sanchez | |
| 2016/0179877 A1 | 6/2016 | Koerner | |
| 2016/0189174 A1 | 6/2016 | Heath | |

OTHER PUBLICATIONS

Oracle.RTM. Database 11g Release 2 is Now Available Sep. 1, 2009, Oracle, http://www.oracle.com/us/corporate/press/032365.
Oracle Database New Features Guide 11g Release 2 Sep. 2015, 78 pages.
Ashdown et al., Oracle Database Concepts 11g Release 2 Sep. 2011, Oracle, toc, Chapter 7.
Chant et al., Oracle Database Performance Tuning Guide 11g Release 2 Jun. 2014, Oracle, toc, Chapters 11, 17.
Strohm, Oracle Clusterware Administration and Deployment Guide 11g Release 2 Jun. 2015, toc, Appendix F.
Anand, The world of Oracle API Feb. 12, 2008, oracleappshub.com, http://www.oracleappshub.com/ebs-suite/the-world-of-oracle-api/.
Tsekouras, Use DBMS_SQLTUNE.IMPORT_SQL_PROFILE to force a hint to a query Sep. 15, 2013, Oracle DBA, http://lefterhs.blogspot.com/2013/09/use-dbmssqltuneimportsqlprofile-to.html.
Oracle Database 11gR2: Clustering—Grid Plug and Play—Online Course NEW 2010, Oracle University, http://education.oracle.com/pls/web_prod-plq-dad/view-pdf?c_org_id=56&c_1-ang=BG&c_id=D64359GC10.
Oracle Real Application Clusters in Oracle VM Environments, Mar. 12, Oracle Sys, https://web.archive.org/web/20120417175948/https://www.oracle.com/technetwork/database/clustering/oracle-rac-in-oracle-vm-environment-131948.pdf.
Romanenko, Oracle RAC 11g Database on Linux Using Virtual Box Dec. 12, lab128.com, http://www.lab128.com/rac_installation_using_vb/article_text.html.
Strohm, Oracle Clusterware Administration and Deployment Guide 11g Release 1, Jun. 2010, 406 pages.
Caffery, Getting Answers with SELECT Feb. 2012, Oracle Magazine, https://blogs.oracle.com/oraclemagazine/getting-answers-with-select.
Moore et al., Oracle Database Online Documentation Library 11g Release 2 Explicit Cursor Declaration and Definition 2014, Oracle, https://docs.oracle.com/cd/E11882_01/appdev.112/e25519/explicit_cursor.ht-m#LNPLS01313.
Feuerstein, Working with Cursors Part 12 in a series of articles on understanding and using PL/SQL Apr. 2013, oracle.com, https://blogs.oracle.com/oraclemagazine/working-with-cursors.
Rich, Oracle Database Reference 11g Release 2, Oracle, https://docs.oracle.com/cd/E11882_01/server.112/e40402.pdf.
Using Python With Oracle Database 11g date unknown [listed in Google Search as Oct. 28, 2009], Oracle Sys, https://www.oracle.com/technical-resources/articles/database/python-with--database-11g.html.
An introduction to machine learning with scikit-learn date unknown, scikit-learn.org, v.0.15 https://scikit-learn.org/0.15/tutorial/basic/tutorial.html.
Recognizing hand-written digits date unknown, sciklit-learn.org, v0.15 https://scikit-learn.org/0.15/auto_examples/plot_digits_classification.ht-ml#example-plot-digits-classification-py.
Reference date unknown, scikit-learn.org, v0.15, https://scikit-kearn.org/0.15/modules/classes.html.
Sklearmensemble.partial_dependence.plot_partial_dependence date unknown, scikit-learn.org, v0.15, https://scikit-learn.org/0.15/modules/generated/sklearmensemble.partial_-_dependence.plot_partial_dependence.html#sklearm.ensemble.partial_dependenc-e.plot_partial_dependence.
Julio.h et al, Anaconda and distributed execution with MPI Jan. 20, 2014, Google Groups, https://groups.google.com/a/continuum.io/forum/#!topic/anaconda/Qde7IgDLGBc.
Release Notes Oct. 15, 2019, anaconda.com, https://docs.anaconda.com/anaconda/reference/release-notes/.
Hastings, PEP 429—Python 3.4 Release Schedule Mar. 18, 2019, python.org, https://www.python.org/dev/peps/pep-0429/.
Lutz et al, Learning Python 1999, O'Reilly, pp. 4, 140, 218.
Binneman, How to Build your Department's Reputation May4, 2009, wordpress.com, https://deonbinneman.wordpress.com/2009/05/04/how-to-build-your-departments-reputation/.
Pang et al., Opinion mining and sentiment analysis 2008, NOW, Foundations and Trends in Information Retrieval vol. 2, pp. 1-135.
Bitext, Differences between Polarity and Topic-Based Sentiment Analysis 16 Jun 16, bitext, https://blog.bitext.com/polarity-topic-sentiment-analysis.

* cited by examiner

DATA ANALYSIS USING NATURAL LANGUAGE PROCESSING TO OBTAIN INSIGHTS RELEVANT TO AN ORGANIZATION

CROSS REFERENCE TO RELATED APPLICATIONS

This Continuation-in-Part application claims priority to U.S. application Ser. No. 14/975,778, filed Dec. 19, 2015, which application is a Continuation-in-Part and claims priority to U.S. application Ser. No. 14/971,885 filed Dec. 16, 2015, now U.S. Pat. No. 10,776,359 issued Sep. 15, 2020, which in turn claims the priority of U.S. Provisional Application No. 62/124,799 filed on Jan. 5, 2015, which all applications & patents are incorporated herein in their entirety by this reference.

BACKGROUND

Business intelligence (BI) is of utmost importance to businesses. Business intelligence involves performing data analytics to answer questions of interest to the business. An example question may be "What is my sales number for this quarter for a certain region." Another question may be "From available data, who are the customers who may likely be defecting to a competitor." In performing data analytics-based business intelligence (DA-BI), it is necessary to gather data from a variety of sources, organize the data, analyze the data, and present the analytics result in a manner that makes sense to the user.

There are existing software applications for performing DA-BI currently. These applications permit the acquisition of data, the organization of stored data, the application of business rules to perform the analytics, and the presentation of the analytics result. In the past, such applications require the use of an expert system integrator company or highly skilled personnel in the IT department (often a luxury that only the largest companies can afford) since these tools require custom coding, custom configuration and heavy customization.

The explosion in the volume of data in the last few years means that the customer now has more data and more variety of data formats to work with. At the same time, customers are demanding more in-depth answers from the available data. This increase in data volume and data formats, as well as the increased need of customers, has created a need to update or change many existing business intelligence applications. However, due to the customized hard coding nature of existing BI-applications, many businesses have not been willing or simply do not have the money and/or time to commit to updating their existing BI system or purchasing a new BI system.

Furthermore, new technologies are now available for data storage, data acquisition, data analysis, and presentation. Big data or cloud computing (whether open-source or proprietary) are some examples of such technologies. Some of these technologies have not yet been widely adopted by the BI industry. Being new, the level of expertise required to make use of these technologies is fairly high since there are fewer people familiar with these technologies. This trend drives up the cost of implementing new BI systems or updating existing BI systems for customers, particularly if the customers desire to make use of the new technologies.

In view of the foregoing, there is a need for a new approach to create and/or update data analytics applications for customers.

SUMMARY

To achieve the foregoing and in accordance with the present invention, systems and methods for the identification of topics, features impacting the topics, and recommendations for improving the topics is provided.

In some embodiments, a set of unstructured data pertaining to an organization is first received. This data may include a set of reviews that include a rating, as well as free form text (comment). This text is analyzed using natural language processing (NLP) techniques to identify topics within the comments. A general and industry or organization specific ontology may be leveraged for identification of the topics. For each topic, a special taxonomy of the words adjacent (within 2 or 3 words) to the topic is used to identify the polarity and severity of the topic. This polarity and severity, for each topic in a given comment, may be used to generate a score for the individual comment.

After the individual topics, with their polarity and severities have been determined, they may be aggregated across all comments to generate an aggregate topic. All aggregate topics are combined to generate an aggregate score for the organization. The aggregate score may be adjusted based upon the total number (or percentage of instance) that a topic occurs in the comments, and organizational priorities. Topics that most severely impact the calculated score may then be identified by ranking the topics, and picking out a set number of most impactful topics.

For these identified topics, a set of related topics, or "features", may be identified. These are topics found concurrent to the topic across many comments. They are causal or correlated to the topic. Form these topics and insights, a set of recommendations may be generated to help improve the overall score (and hence user satisfaction) of the organization as a whole.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1:
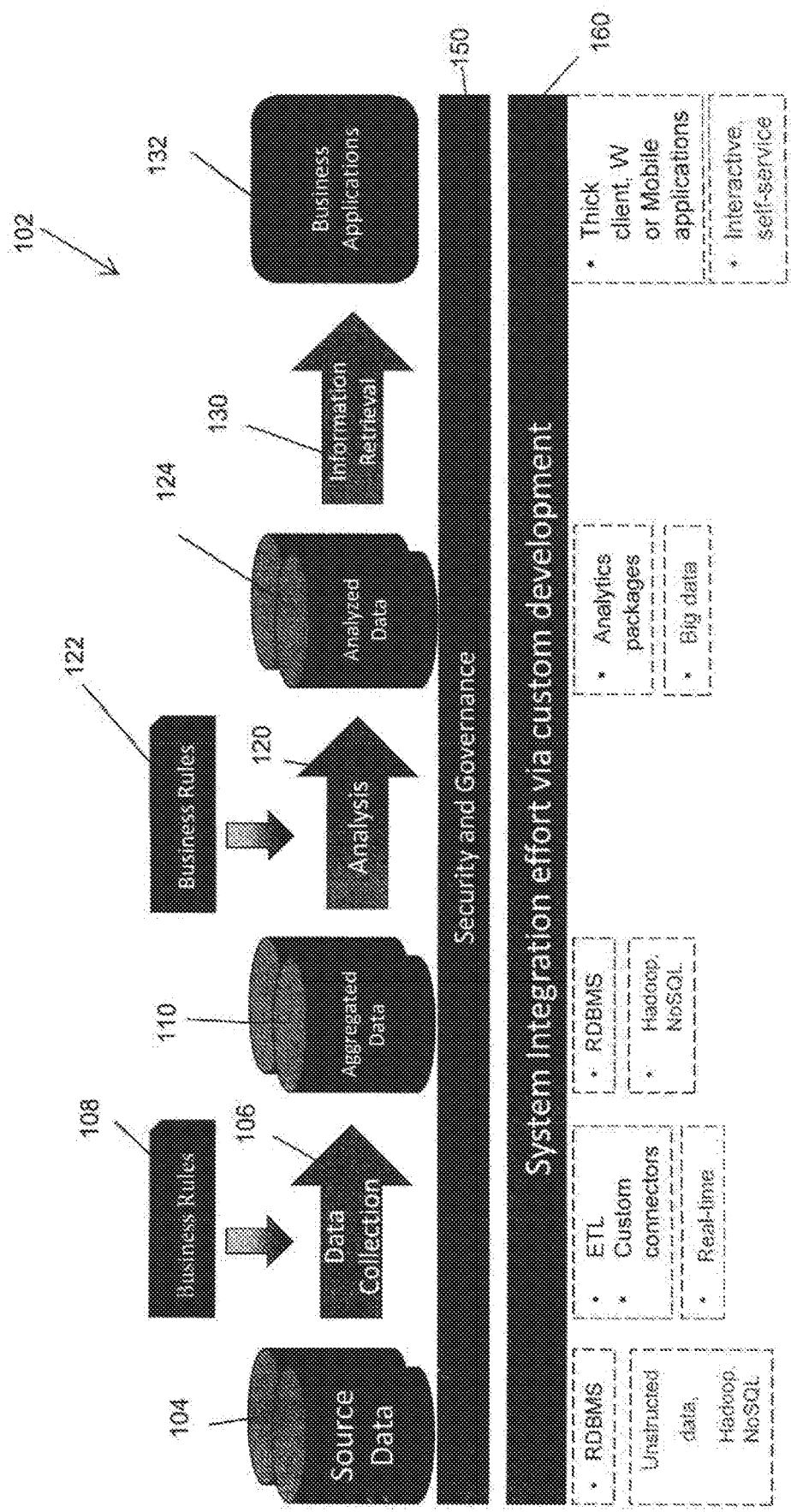
FIG. 1 shows, in accordance with an embodiment of the invention, a typical existing business intelligence (BI) analytics system.

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Embodiments of the invention relate to methods and apparatuses for creating data analysis (DA) systems for generating insights (also known as results) from a plurality of data sources without requiring the designer/implementer of the DA system or the user to understand complicated technology details such as for example coding, big data technology or high-end business analytics algorithms.

In one or more embodiments, there exists a layer, known as a metadata layer, that contains metadata construct pertaining to data definition and design definition for subcomponents of the DA system. The technology details (e.g., what technology is employed to implement a particular subcomponent or to facilitate communication/storage) is generalized and hidden from the designer/implementer and/or the user. The subcomponents communicate via APIs (application programming interface) to facilitate plug-and-play extensibility and replacement.

The metadata construct (which may be a file or library or collection of files/libraries) contains information on the data definition (what data to expect; the format of the data; etc.) as well as the design definition (what to do with the receive data; how to store, organize, analyze, and/or output the data, etc.) as well as the data flow among the subcomponents. Preferably, the metadata construct is created in advance during design time. At execution time, the execution engine receives the BI query from a user, reads the data in a metadata construct that corresponds to that BI query and executes the BI query using data in the metadata construct to enable the subcomponents to retrieve and analyze data as well as output the BI insight.

In one or more embodiments, a user interface, which may be graphical, is employed to create the metadata construct. In one or more embodiments, the metadata construct is an XML, file. The metadata construct represents a standardized manner to communicate with subcomponents of the BI system and contains instructions on how those subcomponents are to act, alone and in coordination with one another, to transform the data from the various data sources into an analysis result such as a business insight. Since the metadata construct is a generalization of the underlying technology, embodiments of the invention allow implementers to create an end-to-end BI application that takes in a BI query and automatically provide the BI insight simply by populating or creating content in the appropriate metadata construct (as well as some light customization for data output format if desired).

In this manner, an end-to-end DA application (such as a business intelligence application) can be implemented without requiring the time consuming hard coding and expensive/scarce knowledge regarding the underlying technologies/algorithms. Furthermore, by allowing subcomponents to be implemented in a plug-and-play manner via APIs, it is possible to re-use or leverage existing analytics tools or parts thereof (such as an existing analysis module) by simply providing an appropriate API for the module and generating the data definition and design definition for it in the metadata construct. This is a huge advantage to customers who may have already invested substantially in existing data analysis infrastructure.

These and other advantages of embodiments of the present invention will be better understood with reference to the figures and discussions that follow.

FIG. 1 shows, in accordance with an embodiment of the invention, a typical existing business intelligence (BI) analytics system. In this application, a business intelligence system is used as an example of a data analytics system but it should not be a limitation and the discussion applies to data analytics systems in general.

A BI system 102 receives data from a variety of data sources 104 in a variety of formats. These data sources may include the corporate transactional systems (such as sales or accounting or customer relations), syndicated data (such as from 3rd party), web-based data (such as social media) and streaming data. The data may be stored in a relational database (RDBM) or in big data-related storage facilities (e.g., Hadoop, NoSQL). With regard to format, the data may be in any format including unstructured, structured, streaming, etc.

Data collection 106 pertains to activities required to acquire the data from the data sources 104. Data acquisition may employ ETL (Extract, Transform, Load) technologies or may employ custom connectors to the individual data sources 102 for example. The data collection may happen in batches or in real time.

During data collection, business rules 108 may apply to pre-filter and/or pre-process the data. For example, some syndicated data may be in a specific format to suit the needs of a particular system unrelated to BI (such as reimbursement data from the reimbursement database of insurance companies, which data may include short-hand alphanumeric coding for common procedures and/or medication) and these formats may need to be converted for more efficient utilization by the analysis component later.

The data collected is then stored in an aggregated data source 110 for ready use by the analysis module. The aggregated data may be stored in a relational database (RDBM) or in big data-related storage facilities (e.g., Hadoop, NoSQL), with its formatting pre-processed to some degree (if desired) to conform to the data format requirement of the analysis component.

The analysis component analyzes (120) the data using business rules 122 and stores the BI insight in analyzed data store 124. The analysis may employ some custom analytics packages or may employ big data analysis techniques for example. At some point in time, the user may desire to know the BI insight and thus information retrieval (130) is performed to obtain the BI insight from the analyzed data store 124 and to present the BI insight to business applications 132. These presentation methods may be self-service or interactive (such as through a webpage that allows the user to sort and organize the data in various ways). The presentation medium may be a thick client, a web or mobile application running on a desktop, laptop, or mobile device for example.

Underlying the above activities is a security and governance subsystem 150 that handles house-keeping and system-related tasks such as scheduling jobs, data access authorization, user access authorization, auditing, logging, etc.

In the past, the implementation of BI system 102 typically involves hard-coding the components, creating custom code to enable the components of FIG. 1 to interoperate and produce the desired BI insight. The system integration effort and custom development (160) require a substantial investment of time and effort during the development, integration, and deployment stages. Because of the rapidly changing technology landscape, a typical company often does not have sufficient IT expertise in-house to build, maintain and/or deploy a BI system if that company desires to utilize the latest technology. Instead, the work is contracted out to integrator firms with special expertise at great cost in each of the development, maintenance, deployment, and upgrade phases.

The hard coding approach makes it difficult and/or expensive to upgrade when new BI insight needs arise and/or when improved technology is available for the tasks of data acquisition, data analysis, and/or data presentation. It also makes it difficult to re-use legacy subcomponents that the business may have already invested in in the past. This is mainly because of both the cost/time delay involved in re-coding a BI system and the predictable scarcity of knowledgeable experts when new technologies first arrive.

Figure 2:
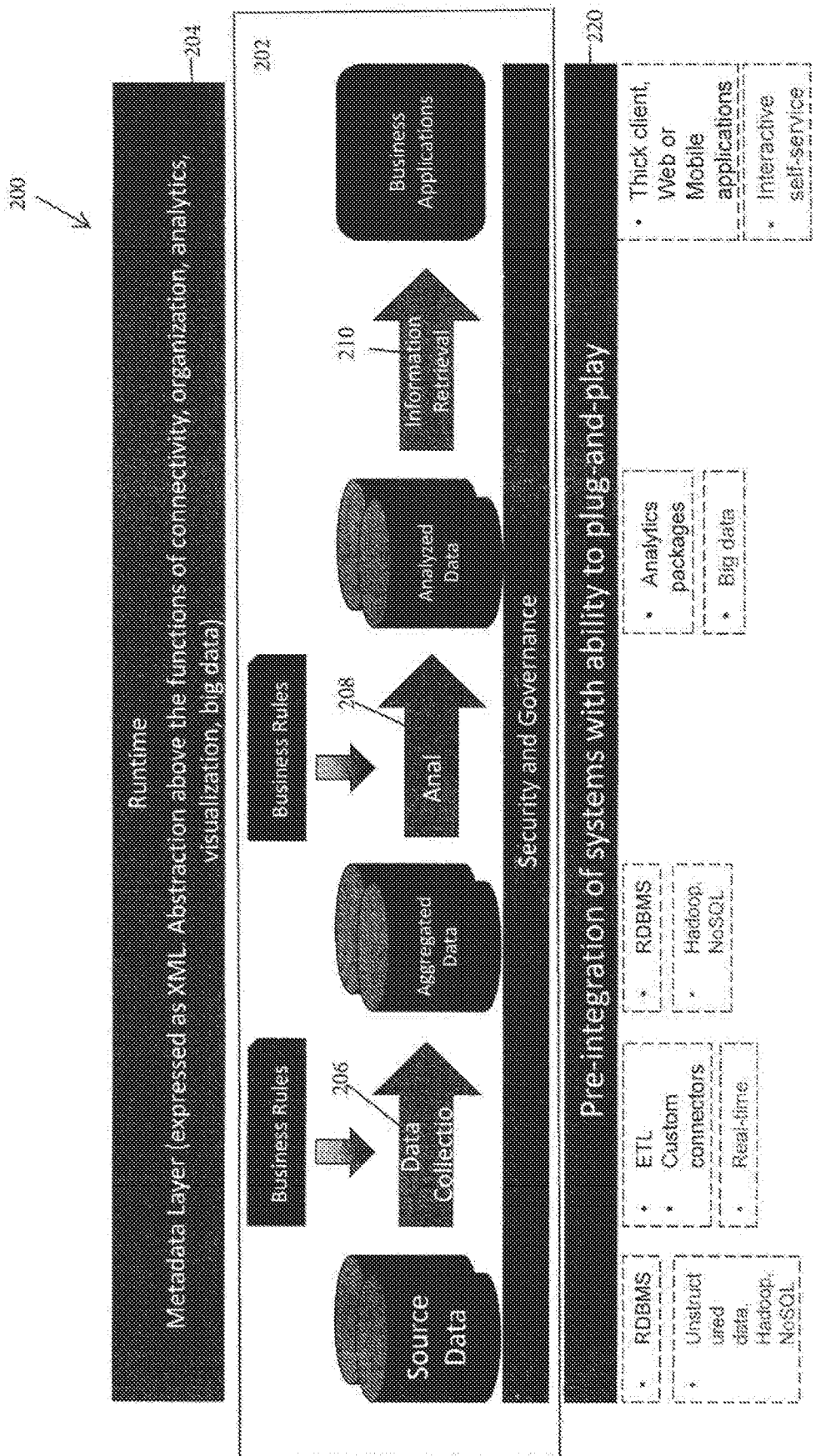
FIG. 2 shows, in accordance with an embodiment of the invention, the conceptual organization of the improved automated-implemented data analysis system (AI-DAS)

FIG. 2 shows, in accordance with an embodiment of the invention, the conceptual organization of the improved automatically-implemented data analysis system (AI-DAS). The conceptual tasks that need to be performed in box 202 are analogous to those discussed in connection with FIG. 1. However, embodiments of the invention pre-integrate (220) the subcomponents (to be discussed later in FIG. 3 and later figures) with plug-and-play capability in order to facilitate their upgradability and extensibility.

More importantly, there exists a layer, known as a metadata layer 204. The metadata may be implemented by a file or library or a collection of files or libraries and contains data pertaining to the data flow among the subcomponents of components implementing the three tasks of BI system 200 (data collection 206, data analysis 208, and analysis result retrieval/presentation 210). The metadata may also include information about data definition and design definition for each of the subcomponents. Generally speaking, data definition pertains to the location where the data comes from and where it is to be outputted, the format of the data, and the like. Design definition generally pertains to the operation in each subcomponent including for example what to do with the inputted data, how to store, organize, analyze, output the data, etc.

The metadata 204 is designed during design time in order to define the operation of the subcomponents and the data flow among the subcomponents, and by extension, the operation of the resulting BI system for a particular type of query. During design time, the designer/implementer is shielded or isolated from the technology details of the subcomponents. The designer/implementer task becomes one of populating the metadata construct with sufficient information to allow each subcomponent to know what data to expect and to output, and how each subcomponent is to behave during execution. In an embodiment, a graphical user interface is provided to assist in the task of filling out the data fields of the metadata. Because the implementer/designer of the BI system only needs to work at the high level of abstraction of the metadata layer, expensive skilled knowledge regarding the newest technology is not required. Further, because the system can be easily reconfigured (simply by creating another metadata) to handle different analysis tasks or accommodate different/substitute subcomponents, re-use of many of the subcomponents is promoted.

At execution time, the BI query from the user is intercepted and a metadata construct (file, library, or set of files/libraries) appropriate to that BI query is retrieved. The execution engine then reads and interprets the data in the metadata in order to know how to utilize the subcomponents to perform tasks to arrive at the BI insight requested by the BI query. Again, the user does not need know the details of the underlying technologies or even the presence/structure of the metadata itself. As long as the user can input a BI query that can be parsed and understood by the BI system, the BI system will automatically select the appropriate metadata construct and will automatically carry out the required tasks using data from the metadata construct and the subcomponents of the BI system.

Figure 3:
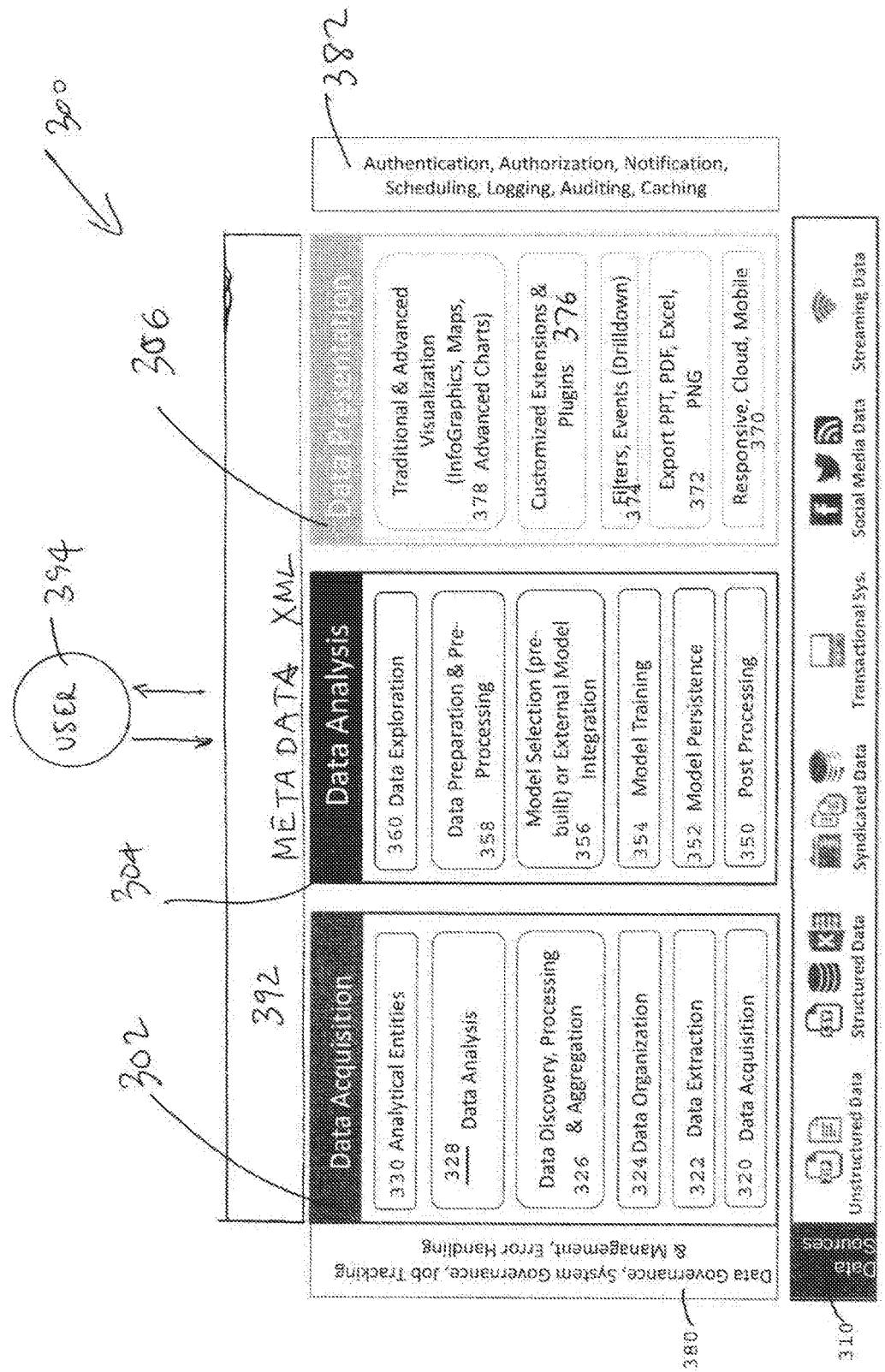
FIG. 3 shows, in accordance with an embodiment of the present invention, the details of one implementation of the automated-implemented data analysis system (AI-DAS) system.

FIG. 3 shows, in accordance with an embodiment of the present invention, the details of one implementation of the automatically-implemented data analysis system (AI-DAS) system 300. AI-DAS 300 includes three main components: Data acquisition, data analysis, and data presentation.

Data acquisition 302 relates to getting the data, organizing the data, extracting the data, storing the data. As shown in box 310, the various data sources include unstructured data (e.g., freeform data such as the text entered by patient comments or doctor/nurse comments), structured data such as data enter into fields of a form, syndicated data such as data purchased or received from third parties, transactional system data such as data directly obtained from the ERP system or the enterprise data store of the company, social media data such as data from Facebook, Twitter, Instagram, and the like. The data may be received in batches or may be streaming data. These are only examples of data sources that may be employed for analysis by the AI-DAS 300.

Within data acquisition component 302, there exist a plurality of subcomponents shown as data acquisition-related subcomponents 320-330. Subcomponent 320 pertains to the task of data acquisition, which relates to how the data is acquired from various sources 310. Subcomponent 322 relates to data extraction, which contains the logic to extract the data sources 310. Subcomponent 324 pertains to data organization, which contains the logic to organize the extracted data. Subcomponent 326 pertains to certain pre-processing of the data. For example, the extracted data is discovered (such as using parsing or artificial intelligence) processed (such as mapping) and aggregated. Splitting and merging of various data items may also be done.

Subcomponent 328 pertain to additional higher level processing of the data, if desired. Subcomponent 330 pertains to grouping data sources into a transactional unit that can be processed as a single entity. For example, the total number of data sources may comprise hundreds of data sources available. However, for a particular BI query, only certain data resources are used. These can be grouped together in a single analytical entity for ease of administration.

Data analysis component 304 relates to analyzing the data and extracting meaning from the aggregated data that is output by data acquisition component 302. Within data analysis component 304, there exists a plurality of subcomponents shown as data analysis-related subcomponents 350-360. Subcomponent 360 relates to data exploration since at this stage, it may not be known what the data contains. Artificial intelligence or pattern matching or keywords may be employed to look for meaning in the data. The data can be prepared and preprocessed in 358 to convert the data into a format for use by the algorithm.

The three subcomponents 352, 354, and 356 represent the machine learning approach that is employed for this example of FIG. 3. In subcomponent 356, the model is selected which may be prebuilt or an external model may be integrated. In subcomponent 354, the model is trained and once the model is selected 356 and trained in 354, the model may be persisted 352 to process the incoming data. Post-processing 350 relates to preparing the data for presentation, which occurs in data presentation component 306.

Data presentation subcomponent 306 relates to how to present the data to the user. The data may be presented using traditional and advanced visualization methods (378) such as infographics, maps, and advanced charts. Legacy presentation tools may also be employed via standard or customized extensions and plug-ins 376. Tool may be provided for the user to filter and to drill down the data, essentially allowing the user to explore the result in 374. The data may also be exported into a desired data format for later use. This is shown 372 wherein the example the formats are PowerPoint, PDF, Excel, PNG. The presentation mechanism can be interactive or static, and presentation data can be sent via the cloud and/or internal network to a laptop, desktop, or mobile device (370).

Subcomponent 380 relates to data governance, system governance, job tracking and management, and error handling. These are tasks related to managing the hardware and software resources to perform the analysis. Subcomponent 382 relates to control of data access and job execution and user access. Thus, there is shown authentication, authorization, notification, scheduling of jobs. Logging, auditing, and intelligent caching of data to improve execution speed are also shown in 382.

A metadata construct 392 is shown interposing between the user 394 and the components/subcomponents of the AI-DAS 300. As mentioned, this metadata contains the higher level abstraction of the subcomponents and allow the AI-DAS to be implemented without knowing the complex underlying technology details.

All the subcomponents shown in each of the data acquisition, data analysis, and data presentation components can be either off-the-shelf, custom created, open-source, or legacy subcomponents. For plug-and-play implementation, these subcomponents preferably communicate using the API model. These subcomponents can be implemented on an internal network, in the cloud using a cloud-based computing paradigm (such as through Amazon Web Services or Google Web), or a mixture thereof. Generically speaking, these are referred to herein as computer resource.

Figure 4:
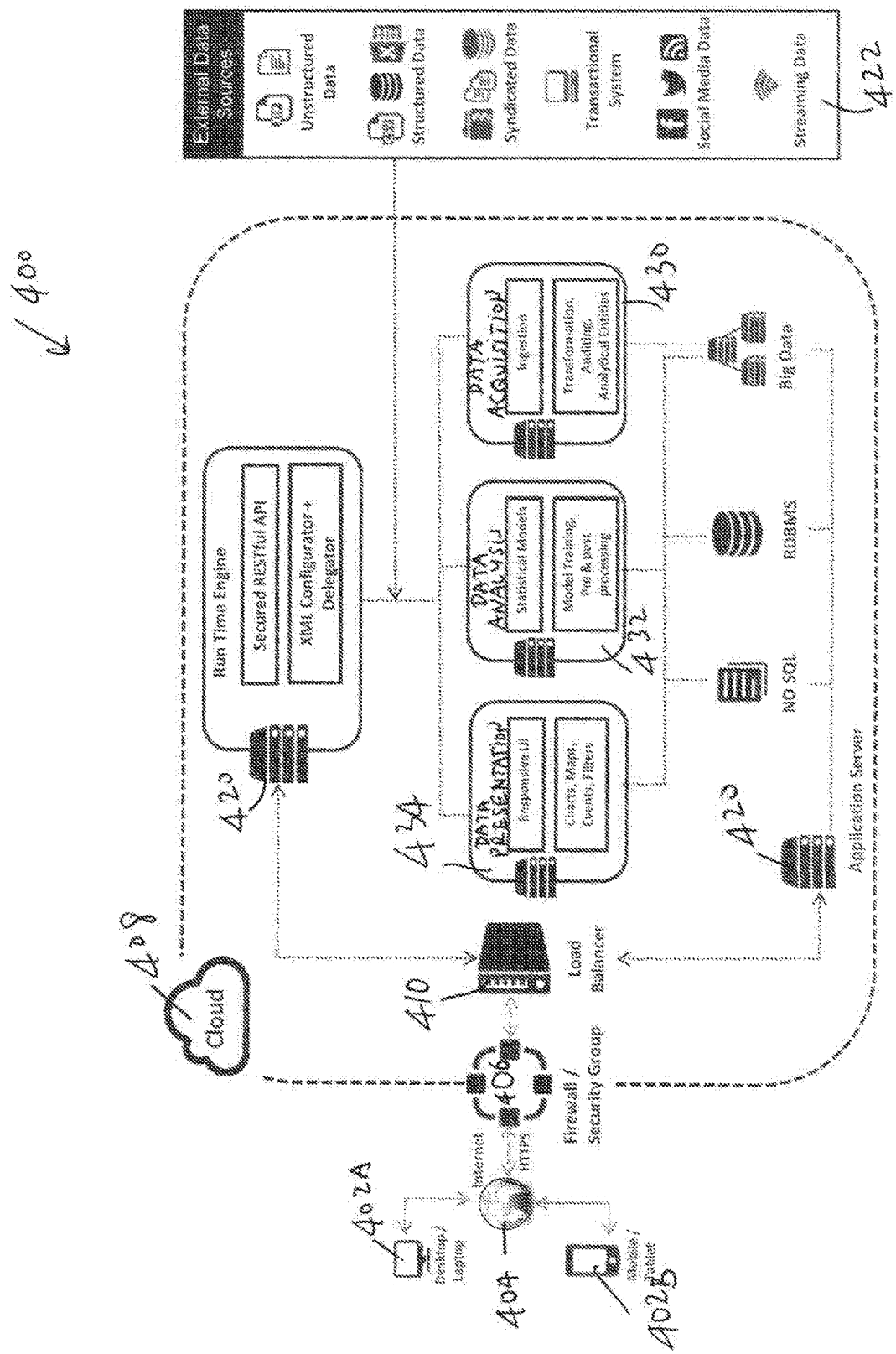
FIG. 4 shows a system architecture of an example AI-DAS implementation.

FIG. 4 shows a system architecture of an example AI-DAS implementation, including user interface devices 402A and 402B (desktop/laptop and mobile devices respectively). These devices can access the AI-DAS system 400 via in the Internet 404 using for example the HTTPS protocol. Firewall/security group 406 and cloud 408 show that components/subcomponents and data storage employed to implement the AI-DAS may reside in the cloud or may reside behind the firewall within a company or can be both.

The AI-DAS operation is governed by a load balancer 410 which load balances multiple copies of the AI-DAS runtime engine 420. For ease of illustration, the multiple implementations of the AI-DAS runtime engine 420 are shown at both the top and the bottom of FIG. 4. At the top of FIG. 4, these multiple instantiations of the AI-DAS runtime engine interacts with the API (such as Secure RESTful API) that governs the communication between subcomponents in the data acquisition component, the data analysis component, and the data presentation component. The AI-DAS runtime engine also reads the metadata (implemented as an XML in the example) and interpret the XML then delegates the tasks specified by the XML to various subcomponents in the data acquisition, data analysis, and data presentation subcomponents.

Data is received from external data sources 422 and is processed via data acquisition subcomponent 430, data analysis subcomponent 432, and data presentation subcomponent 434. The data is processed by data acquisition subcomponent 422 via ingestion module and transformation, auditing, analytical entities. The aggregated and analyzed data is then stored in the appropriate data store (such as Hadoop big data store), relational database RDBMS, or noSQL data store.

The data analysis subcomponent 432 represents the intelligence component and includes therein statistical models and modules related to model training, pre- and post-processing. The data presentation subcomponent 434 includes the various responsive (interactive) user interfaces and may include traditional presentation tools such as charts, maps, events, filters. As shown in FIG. 4, there may be multiple instantiations of each of the components/subcomponents in addition to different instantiations of multiple runtime engines, all of which can be load balanced to horizontally scale the analytics system to accommodate any volume of analytics jobs.

Generally speaking, there are the two separate phases of building and delivering an AI-DAS end-to-end application. One of the requirements is that the subcomponents employ APIs, allowing them to interoperate using an API model and to receive instructions from the execution engine as the execution engine interprets the metadata. Thus, during design time, a designer/implementer may create the metadata XML that includes the data definition and design definition for the subcomponents. Once the design phase is completed, the system is deployed and ready to produce analysis result during execution time.

During execution time (which occurs when a user inputs a query), the metadata XML is selected for the query, interpreted and executed by the AI-DAS engine, which metadata specifies how each subcomponent would behave based on the parameters specified in the metadata. The metadata also specifies the format of the data that the subcomponents exchange among each another, as well as the overall data flow from data intake from multiple data sources to the presentation of the analytic results to the user interface devices.

Figure 5:
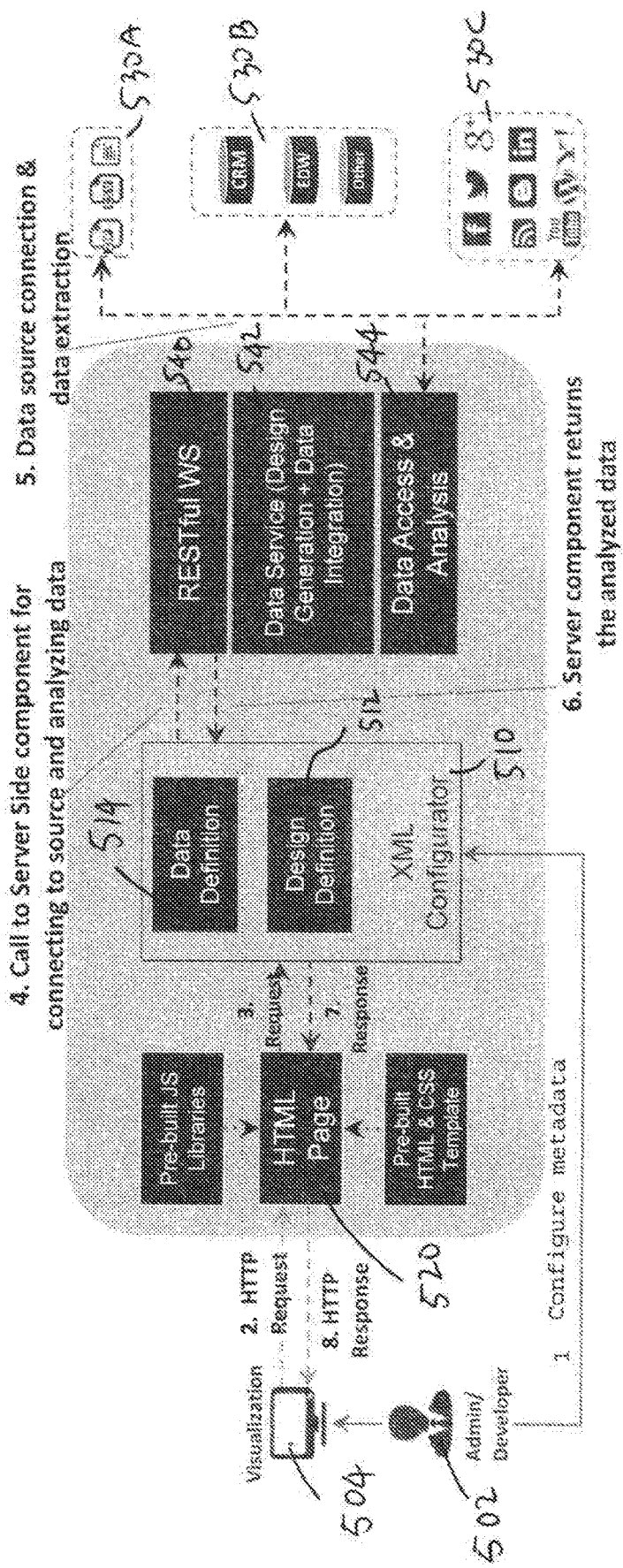
FIG. 5 shows, in accordance with an embodiment of the invention, an example workflow employing the runtime engine in order to perform business intelligence analysis.

FIG. 5 shows, in accordance with an embodiment of the invention, an example workflow employing the runtime engine in order to perform business intelligence analysis. During design time, administrative/developer 502 employs UI device (which may be for example a laptop or desktop computer) 504 to configure the metadata (such as the XML). This is shown as step 1 of FIG. 5. Preferably, a graphical user interface is employed to simplify the task of populating the metadata fields. At this time, any custom HTML templates and custom javascript can also be created to format the output if desired.

With respect to the metadata XML, the admin/developer 502 may define the data. That is the admin/developer may specify where the data comes from and the type of data that is inputted (e.g., free-form, stream, structured, and the like). The admin/developer 502 may also specify the design definition, that is how the data is used in the application. The design definition defines the goal of the data analysis. For example, one goal may be to perform sentiment analysis on conversation data about nurses. Another goal may be to discover the top three hot topics in the unstructured data that is received. Another goal may be to import certain columns in a relational database and run it through a certain model to identify patients who are not satisfied.

The design definition can also specify the manner in which data is outputted. Examples of such specification include the format and the devices and/or data presentation technologies involved. These are shown in 510, 512, and 514 of FIG. 5.

Then during execution time the user may use a UI device to issue a HTTP request (step 2) that is received by the HTML page 520. The HTML page 520 parses the request then issues another request (step 3) to acquire the appropriate associated metadata XML that contains the data definition and the design definition relevant to the instant query.

With this data definition and design definition in the XML, the AI-DAS engine then makes a call to the server-side component for connecting to resources to obtain data and to analyze data. Note that these data sources and the manner in which the data is analyzed are specified by the XML in the data definition and design definition 514 and 512. This is step 4.

In step 5, the data source connections are selected to connect to the appropriate data sources 530A, 530B, and 530C to obtain data for analysis. The analysis is performed by the server subcomponent that employs, in the example of FIG. 5, the RESTful web service 540. Analysis includes performing data service (design generation and data integration) as well as data access and analysis (542 and 544) in accordance with the definition in the XML.

Once data analysis is completed by the AI-DAS server, the server component returns the analyzed data (step 6) and the response (step 7) is provided to the HTML page. The response may be formatted in accordance with the definition in the XML page. The response is then returned to the UI device 504 for viewing by the user and for interaction by the user (step 8)

Figure 6:
FIG. 6 shows some of the technologies involved in implementing the data sourcing, data acquisition, data management, data analysis, data staging, and data extraction.

FIG. 6 shows some of the technologies involved in implementing the data sourcing, data acquisition, data management, data analysis, data staging, and data extraction. Some of these technologies are well-known in distributed computing/big data for storage (such as Hadoop) and for analysis (such as MapReduce, Spark, Mahout). Workflow engine may be provided by OOZIE while system administration may be provided by Ambari and Apache Falcon.

It should be noted that the technology details of FIG. 6 are hidden from the design/implementer during design time since the designer/implementer needs only be concerned with the metadata population and any optional HTML/JS customization for data outputting. These technology details are also hidden from the customer/user during execution since the customer/user only needs to issue a query that can be parsed to obtain the associated XML, and the rest of the analysis and underlying details regarding technology are handled transparently.

Figure 7:
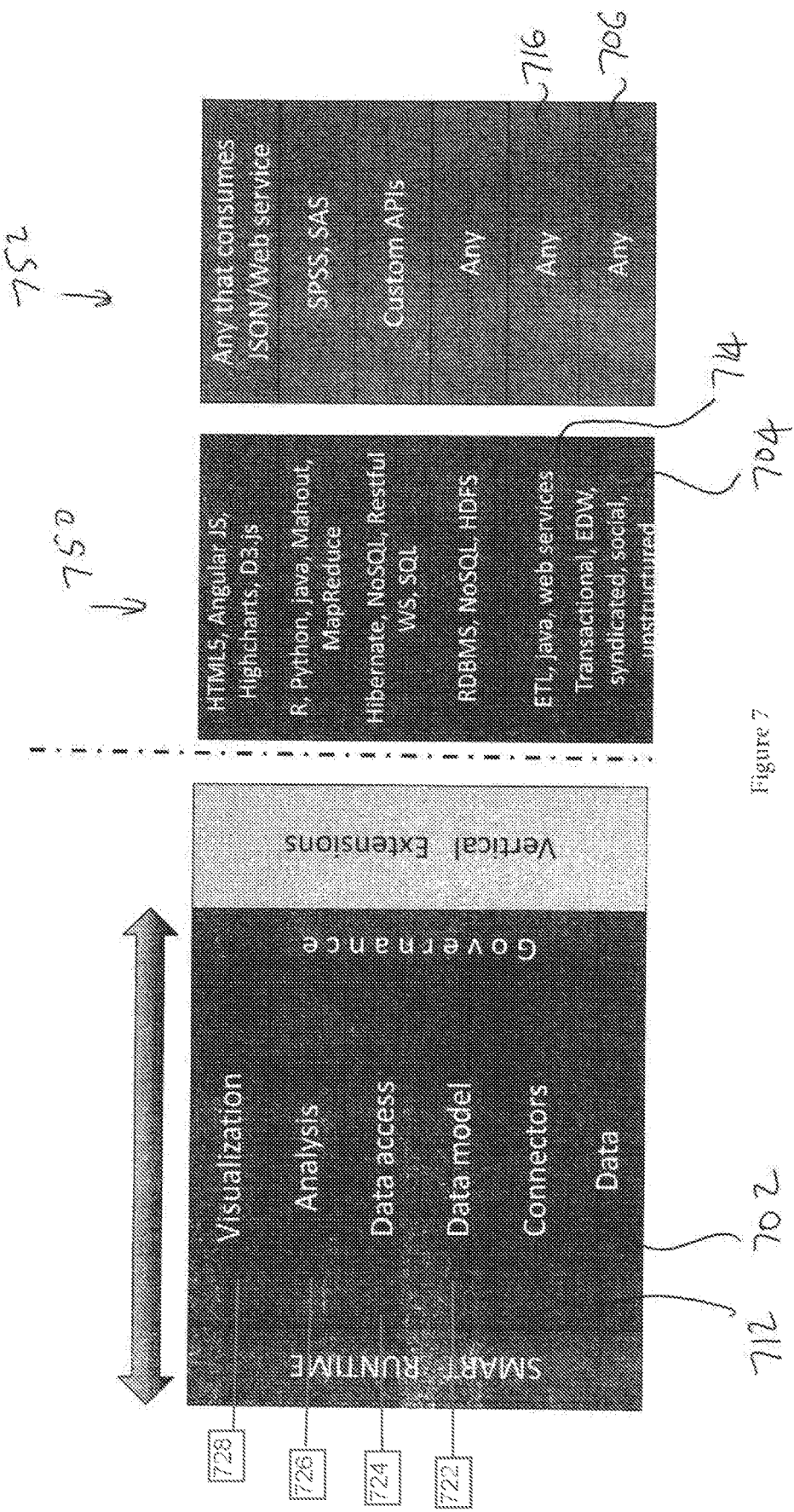
FIG. 7 shows some of the technologies employed in implementing each of the technology stacks in the AI-DAS system.

FIG. 7 shows some of the technologies employed in implementing each of the technology stacks in the AI-DAS system. For example, the data layer 702 may be implemented by (704) transactional, enterprise data warehouse (EDW), syndicated, social, and unstructured data. However, any other alternative data source (706) may be employed.

Connectors layer (712) may be implemented by (714) ETL, Java, Web services. However, any appropriate alternative integration connecting technology (716) may also be employed. The same applies to the data model layer 722, data access layer 724, analysis layer 726, and visualization layer 728. For each of these layers, there is a corresponding list of example technologies in the stack 750 as well as in alternatives/integration 752. One important point to note is since the underlying technology is hidden, the layers (such as data, connectors, data model, data access, and the analysis, visualization) may be implemented by any appropriate technology, including legacy technology.

As can be appreciated from the foregoing, embodiments of the invention renders it unnecessary for the designer/implementer to know or to manipulate complex technology in the implementation, maintenance, or upgrade of a data analysis system. The metadata layer generalizes these complex technology details away and provide standardized, easy-to-implement way of specifying how the DAS system should operate to solve any particular analysis problem.

As long as the subcomponents comply with the API model for interoperability, the underlying technology may be interchangeable on a plug-and-play basis. The ease with which the AI-DAS system can be implemented (due to the abstraction of the complex technology details away from the designer/implementer) encourages exploration and renders implementation, maintenance, and upgrade of a data analysis system substantially simpler, faster, and less costly than possible in the current art.

It is well known that human beings tend to be comfortable exchanging information in narrative form. Conversations or reports, whether oral or written, are examples of narrative information and are a natural paradigm for humans to communicate ever since oral and written communication existed.

Accordingly, narrative information represents one important, albeit voluminous and rather difficult to categorize, source of data for organizations wishing to truly understand the sentiments and attitudes of its stakeholders. Health care institutions are no exceptions, and given the complex nature of health care, much of the valuable information and feedback from its human stakeholders (e.g., patients, doctors, nurses, other health care providers, public members shopping for health care services, public members commenting on the health care institutions in general, etc.) still tend to be in the form of narrative content.

To elaborate, narrative content is unstructured in that the information therein tends not to follow any predefined format. Structured content, on the other hand, stores its data in predefined data fields, with each piece of information in each field clearly informing what the field and the data therein represent.

Information in a tax form is an example of structured content, with the taxpayer's name, address, income, etc. all being associated with appropriate data fields. Forum discussions by public members or blog entries or narrative feedback in a comment form, which may be written in conversational English for example, represent unstructured content wherein there may be no apparent organization to the various pieces of information provided.

In the past, health care organizations have attempted to collect narrative content and employ them to improve service to its patients. For example, the post-discharge procedure often includes an invitation for the patient to write comments on comment cards, or procedures for doctors/ nurses to write a patient discharge summary. Much of this information in the past has been in paper form but with modern technologies, much has also been digitized.

Nevertheless, these various pieces of narrative contents are often filed away in the individual patient's folder, generally contributing little to the understanding of the sentiments and attitudes of the population of the patients as whole toward a specific health care institution or its various aspects of operation. As is usually the case, the only time these narrative contents tend to be reviewed is when there is a dispute with the patient. Only then would the individual patient file be reviewed, and both the patient's narrative feedback and the narrative comments by the medical staff are read to facilitate resolution of the dispute at hand.

Further, the rise of the internet, with its various forums, blogs, social media sites, review sites, and the like also produce narrative contents. Some of these may be highly relevant to a given health care organization although such narrative contents may be generated externally outside of the health care organizations. For example, thousands or millions of people often voice their observations and opinions about the care they or those they know received. These external narrative contents often reflect the sentiments and attitudes of the consuming public (such as the patients or potential patients) toward the health care organization and/or its various aspects of operation. There has yet been a satisfactory attempt at mining these external narrative contents with a goal of using the information therein to improve the health care organization and/or various aspects of its operation.

Other sources of narrative content also exist. For example, third parties often collect data, conduct interviews and compile reports on various health organizations or health care technologies or trends. These third party data sources are often syndicated and can be obtained to understand the sentiments and attitudes of stakeholders toward a given health care organization or an aspect of its operation.

One of the difficulties in assembling and analyzing narrative data is the sheer volume and the apparent lack of organization of data therein. The other reason for the difficulties is more subtle. Even if the narrative data can be collected from the various sources and digitized, unless the proper insight could be obtained from the narrative data, the collection effort is meaningless.

In the past, health care organizations have attempted to form committees of human readers to tackle the narrative information available. Each committee member may be asked to read a subset of the narrative information from one or more sources and to form an opinion about what has been read. The committee members may then meet and decide on the important issues to be addressed based on the narrative information read by its various members. However, such approach is inherently unscalable and relies on the fragile human recollection and impression. It is also inherently unreliable and highly subjective.

What is desired are more objective, scalable, and automated systems and methods for obtaining insights from structured and unstructured information from various sources to drive improvement in the health care organization.

Embodiments of the invention relate to methods and apparatus for aggregating information, both narrative and structured information, from a variety of data sources internal and external to the enterprise, applying natural language processing to analyze the aggregated information with techniques such as sentiment analysis (SA), emotion analysis (EA) and topic analysis (TA) in order to obtain insights that can be used to improve the health care organization or aspects thereof.

In the following discussion, narrative information is emphasized and examples are often directed toward the aggregation and analysis of narrative (i.e., unstructured information). It should be kept in mind, however, that the aggregated data for analysis can include both narrative information and structured information.

In one or more embodiments, the aggregated information from the structured and unstructured data sources is correlated with metadata about the patient healthcare experience (e.g., age, race, location, time of visit, name of hospital, name of department, name of doctors or nurses, nature of visit, etc.). The correlation with metadata permits the obtained attributes (e.g., sentiment, emotion, topics) to be calibrated commensurate with the scope of the business query (e.g., doctors' sentiment about XYZ hospital in general versus patient attitudes about off-hour visits to the emergency room at hospital XYZ).

In the first example business query ("What is the doctors' sentiment about XZY hospital"), the metadata correlation allows the scope of the query to be limited to what are most relevant, i.e., doctors and XYZ hospital. In the second example business query ("What are the patients' attitudes about off-hour visits to the emergency room at hospital XYZ during the winter months"), the metadata correlation allows the scope of the query to be limited to what are most relevant, i.e., patients, off-hour visits to emergency room at XYZ hospital, and winter months).

In one or more embodiments of the invention, advanced data science techniques pertaining to correlation or causation analysis are employed to determine, from the aggregated information and the metadata, the correlation and/or causation of experience issues on the part of patients or other stakeholders. These are the contributing factors, or contributors.

For example, a hospital may wish to know not only which department is disliked by patients but also why. The contributing factors uncovered in the aggregated data may be the distance to the parking lot, wait times, attitude of staff, temperature of the waiting room, the complexity of the check-in procedure. In one or more embodiments, these factors may be weighted to more accurately provide insights. For example, the distance to the parking lot may be given very low weight since it is quite difficult or expensive to change the parking lot situation. On the other hand, the temperature of the waiting room may be given higher weight since more people mentioned being extremely cold and with greater emotion or the temperature setting is something that can be easily changed.

Thus the analysis provides not only an indication of a problem (a department is disliked) but also a possible way to remedy the problem (the reason why patients dislike that department and how to correct). Knowing why and how to correct may also allow that hospital to improve other departments by adopting practices that are well-liked by patients.

Furthermore, one or more embodiments of the invention facilitate correlation of the contributors and/or insights with scores assigned by a third party. Presently, there are organizations (both public and private) that collect data and assign "satisfaction" or "expertise" or "best value" or other scores for hospitals, for specific departments in hospitals, or for a specific doctor or nurse. In the second example above, if a public or private agency rates the emergency room at XYZ hospital as a "three-stars-out-of-five" experience, embodiments of the invention employ the metadata and the aggregated information to attempt to uncover issues or topics of concern regarding the emergency room at XYZ hospital, to narrow down the contributors that are the source of discontent (e.g., too long of a wait during off-hours during the winter months), and provide insights for actionable remedies with the specific goal of trying to improve the score. Over time, such efforts may result in an improved grade or score for the emergency room. Nowadays, such scores may dictate failure or success for a hospital and often translate into real money to be gained or lost. This aspect is discussed later herein.

To elaborate, topic analysis refers to the use of natural language processing to uncover one or more categorical "topics" that occur in one or more documents (such as blog postings, summaries of discharge write-ups, comment card entries, etc.). An example topic may be "parking availability" in the context of the discharge procedure where patients are concerned about the ease with which transportation is available to discharged patients. Another topic may be "doctor manners" in the context of the professionalism (or lack thereof) on the part of the doctors. Another topic may be "emergency room wait duration" in the context of emergency room visits.

Sentiment analysis (also known as opinion mining) refers to the use of natural language processing to identify and extract the polarity (positive, negative, or neutral) toward a particular issue or topic.

Emotion analysis refers to the use of natural language processing to achieve finer granularity grading of the intensity of such polarity. To put it differently, emotions may capture shades of positives or shades of negatives and may include the subjective judgment thereof.

For example, a positive sentiment may encompass the emotions of happy (represented by words such as joyful or glad), pleasant (represented by words such as enjoy or nice), or relief (represented by words such as comfort or solace). A negative sentiment may encompass the emotions of fear (represented by words such as scare, fear or frightening), anxiety (represented by words such as anxious, worry or distress), unpleasantness (represented by words such as dislike, yuck or irksome), or anger (represented by words such as furious or antagonize).

In one or more embodiments, the process of aggregating the narrative and structured data as well as the scoring data from both the internal and external sources employs the earlier discussed data analysis system that partially or wholly utilizes cloud-based and/or big data techniques. Further, in one or more embodiments, the process of analyzing the aggregated data and/or providing insights also employ(s) the earlier discussed data analysis system that partially or wholly utilizes cloud-based and/or big data techniques. However, embodiments of the invention are not so limiting and any other suitable computing system and/or computing resource may be employed.

In an alternate embodiment, the system may starts by using natural language processing (NLP) techniques to identify topics within a set of reviews (unstructured data sets). These reviews may include a rating (score, number of stars, etc.) and freeform text comments. An industry specific ontology, combined with more generalized NLP ontologies, are utilized to identify terms that relate to specific topic categories. In some embodiments, these topic ontologies may be further updated with client specific areas of concern. For example, "pain management" may be a topic that is of particular concern to a given hospital that is known for their management of pain.

Once the topics in a large number of these comments have been identified, the words immediately surrounding the topic are analyzed to determine the polarity (e.g., positivity or negativity) of the topic, as well as the severity of the polarity. A taxonomy associating different phrasing to a severity value is used to determine the severity rating.

Any given comment may include a wide variety of topics, some of which may be positive and other's negative, to varying degrees. These topics, and corresponding polarities and severities, are aggregated for the comment/unstructured data source, and are used to generate a composite score for the organization being reviewed. In some select embodiments, these topics and severities may then be adjusted by normalizing this calculated score versus the overall score/star value supplied by the reviewer.

For example, two users may have a review complaining of the "quietness" within the waiting room of a hospital. Similar verbiage may have been employed, resulting in the topic being "noise level", polarity being "negative" and the severity being 0.8 (out of an exemplary scale of 0-1.0). However, one user may have given the hospital a rating of 3 out of 5 stars, whereas the other user may have rated the hospital as 2 out of 5 stars. The severity of the topics may thus be adjusted lower, as a linear function of the overall rating. In contrast, for a positive polarity topic, severities may be adjusted higher, in a linear fashion based upon overall ratings. Thus, for this overly simplified example, the first user's severity may be adjusted to 0.5, whereas the second user's severity would only be reduced to a value of 0.7 based upon their ratings. It should be noted, that this example is an extreme simplification of the normalization process, using a single variable topic. For most comments, many topics of varying polarity and severity are present. In such instances a multi-variable analysis of the various topics and overall score may be applied to adjust the specific severities accordingly. In some cases, a best fir curve between the calculated score for the comment (based upon an aggregate average of topics by polarity and severity) to the actual supplied score is first performed. The severities are then adjusted by the offset between the calculated score and the received score. For example, if the topics include "quiet-negative-0.8", "wait time-positive-0.4", and "cleanliness-positive-0.5" the final calculated score may be 0.03 (an average between −0.8, 0.4 and 0.5). A rating in a review of 3 stars may be considered 0.0. A five star rating may equate to 1.0 and a one star rating may equal −1.0. So a score of 0.03 is marginally higher than a three star rating. However, for this reviewer, a total rating of 2 stars was provided (−0.5 score). The offset between the calculated score and the actual score is −0.53. Divided by the three factors, each score must be adjusted down 0.18 accordingly. So the final severities for these three factors may in fact be −0.98, 0.22 and 0.32 accordingly. This is of course but one way of adjusting the scores during normalization. Other, more complex, algorithms may likewise be employed for this normalization step.

These normalized topics (with attendant polarities and normalized severities) may be aggregated between all users to generate an overall score for the organization, and a breakdown of which topics impact the organization score, and the degree that they impact the overall score. The aggregated topics level factors that impact the overall score, may be further adjusted based upon the total number of times a given topic has been mentioned in the various comments, the number of the comments that were either positive or negative, multiplied by a weight based upon the severity of sentiment, and further based upon input from the specific organization. For example, as noted before, a particular hospital may be known for their pain management. The organization may choose to place a premium on the topic "pain management" in the calculation of their overall score.

The topics that impact the overall score may then be ranked, and those topics that impact the overall score the most may be flagged for the organization. Features (other topics) that impact the topics that most impact the score are also identified automatically, by correlating the concurrence of the topics across multiple comments, using machine learning techniques. These features, or insights, may likewise be supplied to the organization for review.

For example, it may be noted that "noise level" is identified between all the topics as being a large negative factor to the overall score calculation. The system also identifies that the topic "construction is causally, or at least correlated, to the topic of "noise level". This topic of "construction" is flagged as a feature/insight that impacts the negative attribute/topic of "noise level". Thus, for the organization, it is useful to know not only that noise is a large factor impacting their approval scores (satisfaction score), but that the construction is a cause for this discontent.

Additionally, added insights on ways to improve these topics/features may be supplied to the organization. This may include leveraging machine learning models, or via human intervention. In some embodiments, the computer system may correlate the feature against known "common" recommendations to improve the identified feature. For example, for the feature of "cleanliness" the recommendations may include repainting the building interior with lighter paints, increasing custodial efforts, and increased waste receptacle locations in frequented areas. In some embodiments, these 'common' recommendations are set by a user for each topic/feature within the ontology. Other times, the human input for recommendations may be leveraged to train the machine learning model to generate appropriate recommendations in the future. After the machine supplies a listing of possible recommendations they may be directly supplied to the organization, or in alternate embodiments, be curated by a user to provide on-point, specific recommendations to the problems the organization is experiencing.

In the above example, construction was identified as the feature causing the discontent to the noise level (which in turn was identified as a major influencer in the overall score of the organization). The insight generated for this feature may include warning the visitors that there is construction present (as to limit the shock of the experience), increase noise barriers, or limit the construction to times when fewer patients are present, for example. In this manner, an organization may avoid the costly and labor intensive process of manually reviewing comments to identify areas of improvement, and rather may receive areas/topics where improvement would have the largest impact of user satisfaction, the reasons these topics are rated so negatively, and recommendations on what to do to improve the topic, and therefore increase user satisfaction in the most efficient manner possible.

The features and advantages of embodiments of the invention may be better understood with reference to the figures and discussions that follow.

Figure 8:
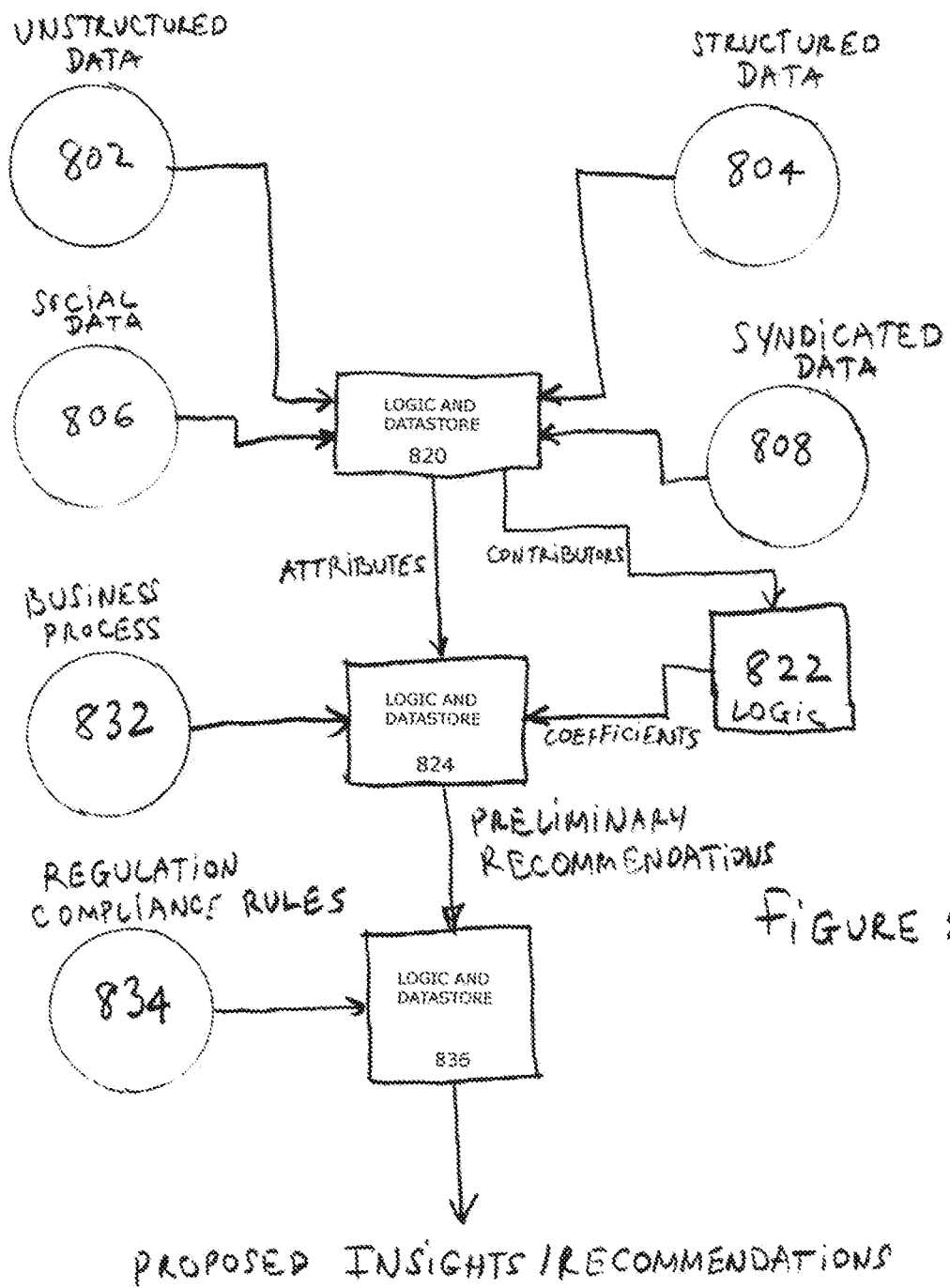
FIG. 8 shows, in accordance with an embodiment of the invention, a data flow representation of the Insight Generation Engine (IGE)

FIG. 8 shows, in accordance with an embodiment of the invention, a data flow representation of the Insight Generation Engine (IGE). The insight generation engine, as discussed, ingests structured and more importantly unstructured narrative data from various sources to form aggregated data. The aggregated data is then processed using natural language processing (NLP) to ascertain attributes and contributors. These attributes can be in the form of sentiment (i.e., positive, negative, or neutral), emotions, topics (e.g., trend, hot topics, topics specified to be important to the organization). These attributes are correlated with metadata to allow the business query to be calibrated with respect to any metadata parameter (e.g., by age, by location, by hospital, by department, by time, etc.) for relevance.

The contributors are factors that are analyzed to be correlated with or to be the cause of the attributes. These attributes and contributors can be processed to provide actionable insights and/or recommendations to improve. These contributors and/or insights can also be further correlated with scoring systems to provide insights into how to improve specific scores of interest.

Data source 802 is an unstructured internal data source, representing for example narrative data from sources internal to the organization. Examples include, without limitation, post-discharge write-ups by doctors or nurses, patient feedback via comment cards, surveys, transcripts of call center conversations with patients, transcripts of conversations or feedback collected by marketing or CRM (client relations management) systems, and the like. The data may be collected and digitized in unstructured data source 802.

Data source 804 is a structured internal data source, representing the structured data collected by the organization. Examples include, without limitation, data from patient management databases, call center records, insurance databases, data from various enterprise resource planning and other enterprise data stores, and the like. Much of this data is already digitized or can be digitized and stored in structured data source 804.

Social data source 806 is a data store of social, forum, and/or blog unstructured data. Examples include, without limitation, posts in forums, blogs, or websites that focus on health care, information from general social media sites on the internet such as Facebook or Twitter or Instagram.

Syndicated data source 808 is a data store of third party data that provides raw or filtered data or processed data that may be of interest to the health care organization. Examples include, without limitation, news articles, published reports, private data compilations, rankings, scorings, surveys, and the like. Syndicated data source 808 may be either structured or unstructured.

Data sources 802-808 are only examples and should not be construed to be limiting of the sources or types of data that can be employed by embodiments of the IGE. Generally speaking, unstructured and structured data from these data sources 802-808 and others may be aggregated in logic and datastore block 820. In logic and datastore block 820, the data is aggregated, pre-processed in preparation for analysis by natural language processing (NLP) techniques. As the term is employed herein, natural language processing may include the use of statistical and/or machine learning and may encompass the fields of text analysis as well as other computational linguistics techniques. NLP is a well-established field and will not be further elaborated here.

The outputs of block 820 are key attributes and key contributors. Key attributes include such things as sentiment, emotions, topics, all of which may be calibrated to the metadata values (e.g., attributes for the department, for the whole hospital, for specific days, for specific group of patients or doctors, etc.). Sentiment may be positive, negative, or neutral. Emotion represent the subjective representation of the intensity of the sentiment, as discussed earlier (e.g., hate, avoid, accepting, satisfied, happy, elated, ecstatic intensity gradations). Topics can be analyzed for trending topics, the top (N) topics discussed, or the topics of special interest to the business, for example.

Key contributors are the variables that have been uncovered to be deemed correlated with or likely to be the cause of the attributes discovered. These are aspects of the actual experiences or perceptions of the stakeholders that give rise to the attribute. As discussed earlier, the attribute of "hate the emergency room" may be contributed by (e.g., associated with the contributors) distance to parking lot, complexity of check-in procedure, attitude of nurses, temperature of waiting room, and the like if these are present in the aggregated data in 820.

Key contributors are provided to logic block 822 to derive coefficient factors, essentially allowing the contributors to be weighted. The factors to consider in assigning weights include the practicality of making changes to the experience contributor variable, the frequency the contributor variable was mentioned in the aggregated data, the relevance of that contributor variable, etc. Thus if the temperature of the waiting room was mentioned many times but the attitude of nurses was mentioned only once or twice, the room temperature contributor variable may be given a greater weight than that associated with the attitude-of-nurses contributor variable.

The coefficient factors are then provided to logic and datastore block 824, where they are processed with the key attributes from block 820 and with business process considerations from block 830 to form preliminary insights. These are the insights or recommendations that are suitable given the business process considerations (832) of the organization. In other words, the analysis includes business process considerations to ensure that insights or recommendations provided are actionable (i.e., practical and/or implementable given the constraints of the business processes available to the organization). The business process data may include for example procedural constraints, structural constraints, time constraints, human resource constraints, budget constraints, etc.

The preliminary insights may be analyzed (logic and datastore block 836) with data in regulation data source 834. Regulation data source 834 represents the data store for compliance rules regarding patient care, patient privacy, record keeping, etc. Health care is a highly regulated business and the analysis of the preliminary insights together with the compliance rules ensures that the resulting proposed insights or proposed recommendations comply with the compliance rules.

Logic block 840 represents audit/improvement data that address inefficiencies, issues, or concerns. This data may come from, for example, audit processes or may be independently proposed ideas that are derived independent of the aggregated data. The audit/improvement data may be fed into logic and datastore block 836 to be analyzed together with the preliminary insights/recommendations (from logic and datastore block 824) and the compliance data (from block 834) to further tune the proposed insights/recommendations.

The insights/recommendations may then be provided to interested persons and/or entities (e.g., department, line of business) for consideration to improve the organization.

Figure 9:
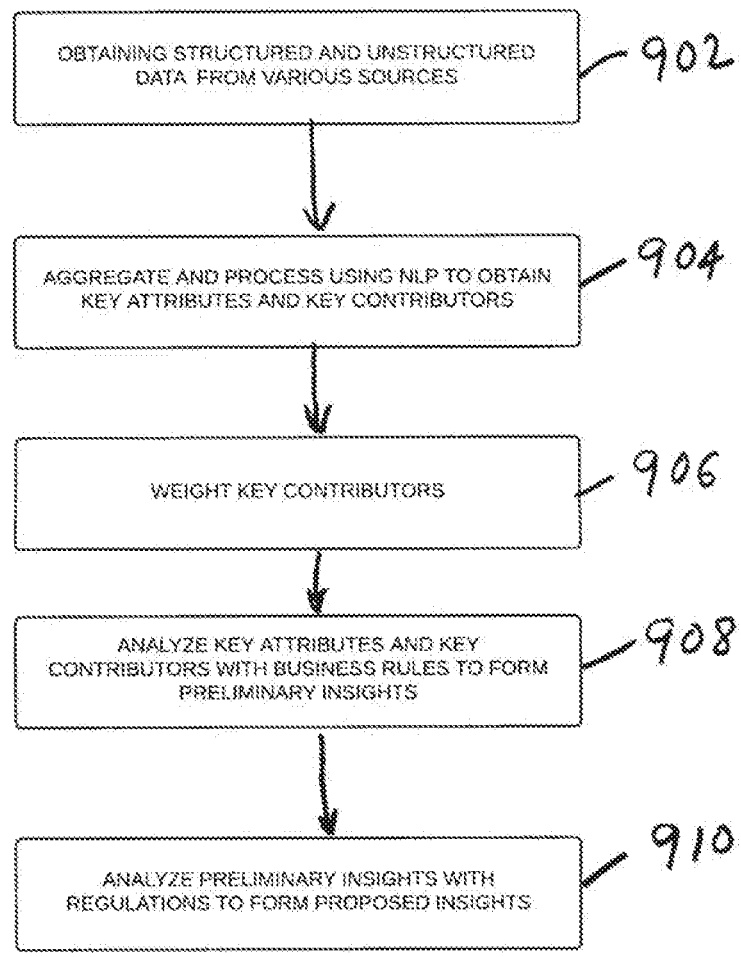
FIG. 9 shows, in accordance with an embodiment of the invention, the steps for deriving insights/recommendations from the structured and unstructured data.

FIG. 9 shows, in accordance with an embodiment of the invention, the steps for deriving insights/recommendations from the structured and unstructured data. In step 902, the structured and unstructured data is obtained from various data sources. In step 904, the structured and unstructured data is aggregated and processed using NLP to generate the key attributes and key contributors. The key contributors are weighted to provide coefficient factors in step 906.

In step 908, the weighted contributors and the attributes are processed together with the business processes to form preliminary insights/recommendations. In step 910, the preliminary insights/recommendations are further processed together with the compliance/regulatory rules and/or any audit/improvement data to form the proposed insights/recommendations.

It should be noted that the outputs of one or more of logic blocks 820 (key attributes or key contributors), 822 (weights/coefficients), 824 (preliminary insights/recommendations) or 826 (proposed insights/recommendations) may be provided as outputs on their own to interested persons or entities in the organization. For example, a certain department may be interested in certain key attributes and/or contributors without necessarily wanting to receive the preliminary insights/recommendations (out of block 824) or the proposed insights/recommendations (out of block 826). As another example, a certain person in the organization may be interested in receiving the preliminary insights/recommendations without necessarily wanting to receive the full proposed insights/recommendations (out of block 826).

In one or more embodiments, the key attributes and/or contributors and/or the insights/recommendations may be analyzed in view of scores from external data sources to provide recommendations on how to improve the score for a given department or aspect of hospital operation, for example. In one example, an organization known as CMS (Center for Medicare and Medicaid Services) provides monetary incentives for hospitals to improve patient satisfaction by awarding money to hospitals that are rated high by patients.

Correlating a hospital that is rated high in a given area (e.g., emergency response) with the attributes and contributors relevant to the emergency room of that hospital, which attributes and contributors being uncovered from the aggregated data, may give decision makers in another hospital an understanding as to why that high-scoring hospital received such high scores from patients in the emergency response area. The understanding of the attributes and contributors that correlate to high scores for emergency services for hospital A can provide data-driven, actionable recommendations for improvement in hospital B, allowing hospital B to make changes that are likely to elicit analogous favorable sentiments and emotions from its patients. As a result, the satisfaction score for emergency services for hospital B may be improved.

In one or more embodiments, the uncovered key attributes and/or contributors across hospitals may allow a given hospital to benchmark itself (i.e., determine how well it is thought of by the stakeholders). For example, a hospital may be interested from the internal/external chatter and other data from doctors with respect to how well it is paying its doctors relative to other hospitals. As another example, a hospital may be interested in knowing whether it is ranked in the top 10% by patients in a given area (e.g., cosmetic surgery). By aggregating structured and unstructured data across hospitals and perform NLP on the aggregated data, the information can be analyzed for such benchmarking purposes if desired.

As can be appreciated from the foregoing, embodiments of the invention provide a data-driven approach for obtaining attribute and contributor data, and ultimately actionable insights from the structured and unstructured data from various sources. The use of natural language processing permits the unstructured data to be mined to obtain relevant attributes and associated contributors, thus making use of a voluminous resource of data that has thus far been judged to be too subjective, too unorganized or too difficult to analyze.

By analyzing the aggregated data with business rules and/or regulatory compliance rules, practical actionable insights and recommendations are possible. The ability to analyze the data across organizations permit benchmarking. Further, the ability to correlate the uncovered attributes and contributors with scores from other scoring mechanisms results in actionable insights/recommendations that can be used to improve the scores.

While this invention has been described in terms of several preferred embodiments, there are alterations, permutations, and equivalents, which fall within the scope of this invention. For example, it is possible to analyze the attributes/weighted contributors with the regulatory rules to form the preliminary insights/recommendations prior to analyzing with the business rules to form the proposed insights/recommendations. The invention should be understood to also encompass these alterations, permutations, and equivalents. It should also be noted that there are many alternative ways of implementing the methods and apparatuses of the present invention. Although various examples are provided herein, it is intended that these examples be illustrative and not limiting with respect to the invention.

What is claimed is:

1. A computer-implemented method for obtaining insights from unstructured data pertaining to an organization, comprising:
    storing information in a standardized format about a set of topics in a network-based non-transitory storage devices having a collection of scores stored thereon;
    providing remote access to users over a network so any one of the users can update information about at least one of the topics in real time through a graphical user interface, wherein the one of the users provides the updated information in a non-standardized comment, wherein the non-standardized comment includes an overall score and unstructured data including text;
    converting, by a server, the non-standardized information into a standardized format by:
        processing the unstructured data using natural language processing to generate a set of topics;
        identifying a polarity and a severity of the topics in each individual comment normalizing the severity for each topic of the topics by a multivariate analysis of all topics in the comment against the overall score for the comment:
        wherein a sentiment is associated with a polarity;
        calculating a topic level factor for each individual topic by aggregating each individual topic by the polarity and normalized severity across all users;
        and adjusting the topic level factor based upon the total number of times a given topic is mentioned in the comments and multiplied by a weight based upon the severity of the sentiment and the topic input from the specific organization;
    ranking the topics, from highest to lowest, based upon their adjusted calculated topic factor identifying a set number of the highest ranked topics; and identifying features that are correlated to the identified highest ranked topics;
    automatically generating a message containing the updated information about the topic by the server whenever updated information has been stored; and
    transmitting the message to the organization over the computer network in real time, so that the organization has immediate access to up-to-date topic information.

2. The computer-implemented method of claim 1, wherein the topics are generated using an organization specific.

3. The computer-implemented method of claim 1, wherein the calculating the score for the comment is an average of the topics by severity and polarity.

4. The computer-implemented method of claim 1, further comprising adjusting the severity for each topic, aggregated over all comments, by a number of occurrences, an average ranking of the organization, and feedback from the organization.

5. The computer-implemented method of claim 1, wherein the identifying features is performed by identifying common topics in multiple comments.

6. The computer-implemented method of claim 1, further comprising outputting the highest ranked topics and features correlated to the highest ranked topics to the organization.

7. The computer-implemented method of claim 1, further comprising generating at least one recommendation to improve the identified features.

8. The computer-implemented method of claim 7, wherein the recommendation is generated by a third party reviewer.

9. The computer-implemented method of claim 7, wherein the recommendation is generated by the computer system comparing the identified features to a plurality of recommendations and then curating the plurality of recommendations by a third party reviewer.

10. A nonvolatile memory product which when implemented on a computer system causes the computer system to the steps of:
    storing information in a standardized format about a set of topics in a network-based non-transitory storage devices having a collection of scores stored thereon;
    providing remote access to users over a network so any one of the users can update information about at least one of the topics in real time through a graphical user interface, wherein the one of the users provides the updated information in a non-standardized comment, wherein the non-standardized comment includes an overall score and unstructured data including text;
    converting, by a server, the non-standardized information into a standardized format by:
        processing the unstructured data using natural language processing to generate a set of topics;
        identifying a polarity and a severity of the topics in each individual comment normalizing the severity for each topic of the topics by a multivariate analysis of all topics in the comment against the overall score for the comment:
        wherein a sentiment is associated with a polarity;
        calculating a topic level factor for each individual topic by aggregating each individual topic by the polarity and normalized severity across all users;
        and adjusting the topic level factor based upon the total number of times a given topic is mentioned in the comments and multiplied by a weight based upon the severity of the sentiment and the topic input from the specific organization;
    ranking the topics, from highest to lowest, based upon their adjusted calculated topic factor identifying a set number of the highest ranked topics; and identifying features that are correlated to the identified highest ranked topics;

automatically generating a message containing the updated information about the topic by the server whenever updated information has been stored; and transmitting the message to the organization over the computer network in real time, so that the organization has immediate access to up-to-date topic information.

11. The nonvolatile memory product of claim 10, wherein the topics are generated using an organization specific.

12. The nonvolatile memory product of claim 10, wherein the calculating the score for the comment is an average of the topics by severity and polarity.

13. The nonvolatile memory product of claim 10, further comprising adjusting the severity for each topic, aggregated over all comments, by a number of occurrences, an average ranking of the organization, and feedback from the organization.

14. The nonvolatile memory product of claim 10, wherein the identifying features is performed by identifying common topics in multiple comments.

15. The nonvolatile memory product of claim 10, further comprising causing the computer system to perform the step of outputting the highest ranked topics and features correlated to the highest ranked topics to the organization.

16. The nonvolatile memory product of claim 10, further comprising causing the computer system to perform the step of generating at least one recommendation to improve the identified features.

17. The nonvolatile memory product of claim 16, wherein the recommendation is generated by a third party reviewer.

18. The nonvolatile memory product of claim 16, wherein the recommendation is generated by the computer system comparing the identified features to a plurality of recommendations and then curating the plurality of recommendations by a third party reviewer.

* * * * *